US006555138B1

(12) United States Patent
Karlsson et al.

(10) Patent No.: US 6,555,138 B1
(45) Date of Patent: Apr. 29, 2003

(54) POLYETHYLENE GLYCOL MATRIX PELLETS FOR GREASY, OILY OR STICKY DRUG SUBSTANCES

(75) Inventors: Christer Karlsson, Lindome (SE); Per Johan Lundberg, Mölndal (SE); Adam Rosinski, Göteborg (SE); Malin Söderbom, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/214,317

(22) PCT Filed: Nov. 18, 1998

(86) PCT No.: PCT/SE98/02090

§ 371 (c)(1),
(2), (4) Date: Jan. 4, 1999

(87) PCT Pub. No.: WO99/27913

PCT Pub. Date: Jun. 10, 1999

(30) Foreign Application Priority Data

Nov. 28, 1997 (SE) .................................. 9704401

(51) Int. Cl.⁷ ........................ A61K 9/16; A61K 31/66
(52) U.S. Cl. ................. 424/489; 424/489; 424/484; 424/486; 424/481; 424/465; 424/485; 514/108; 514/102; 514/18; 514/609
(58) Field of Search ................. 424/464, 486, 424/465, 485, 474, 481, 489, 484; 514/102, 108, 18, 609

(56) References Cited

U.S. PATENT DOCUMENTS

| | | | | |
|---|---|---|---|---|
| 2,699,054 A | | 1/1955 | Conover | 260/559 |
| 4,828,836 A | * | 5/1989 | Elger et al. | 424/419 |
| 5,051,261 A | * | 9/1991 | McGinity et al. | 424/464 |
| 5,071,642 A | * | 12/1991 | Lahr et al. | 424/474 |
| 5,431,920 A | * | 7/1995 | Bechard | 424/450 |
| 5,876,754 A | * | 3/1999 | Wunderlich et al. | 424/489 |

FOREIGN PATENT DOCUMENTS

| | | | | |
|---|---|---|---|---|
| DE | 454386 | | 1/1928 | |
| DE | 557670 | | 9/1993 | |
| EP | 0317780 | * | 5/1989 | A61K/31/44 |
| EP | 0701815 | | 3/1996 | |
| GB | 1440832 | | 6/1976 | |

OTHER PUBLICATIONS

USP Dictionary 1997, pp. 30, 294, 436.*
El–Egakey et al 1974, 29(4), 286–290 (abstract only).*
Merck Index entry No. 9337: *Tetracycline* The Merck Index, 12$^{th}$ Ed., pp. 1571–1572, Merck Research Laboratories (1996).

* cited by examiner

*Primary Examiner*—Russell Travers
*Assistant Examiner*—S Sharareh
(74) *Attorney, Agent, or Firm*—White & Case LLP

(57) ABSTRACT

A drug delivery system for oral administration in solid dry form of greasy/oily/sticky substance(s) and pharmaceutically active substance(s) or pharmaceutically active substance(s) which itself/themselves is/are greasy/oily/sticky) characterized by having a plurality of solid, polymeric matrix beads comprising considerable amounts of greasy/oily/sticky substances and having fast release characteristics and a process for the preparation of such solid, polymeric matrix beads comprising greasy/oily/sticky substances.

15 Claims, No Drawings

POLYETHYLENE GLYCOL MATRIX PELLETS FOR GREASY, OILY OR STICKY DRUG SUBSTANCES

This application is a 35 U.S.C. §371 national phase application of PCT international application PCT/SE 98/02090 filed on Nov. 18, 1998 which claims priority to Swedish application 9704401-0, filed Nov. 28, 1997.

FIELD OF THE INVENTION

This invention relates to a pharmaceutical dosage form comprising solid, polymeric matrix beads for oral administration comprising considerable amounts of greasy, oily or sticky (greasy/oily/sticky) substances and a pharmaceutically active substance alternatively considerably amounts of greasy, oily or sticky pharmaceutically active substances and where the new dosage form is further characterized by having fast release characteristics.

BACKGROUND OF THE INVENTION

In many therapeutic areas the need for incorporating absorption enhancers (e.g. glycerol esters for increased absorption of heparin or heparin fragments or derivatives as described in WO 95/00152 to Pharmacia), solubilizing agents (like polyethoxylated hydrogenated castor oils for felodipine as disclosed in EP 0249587 to AB Hässle), suspending agents (e.g. soybean oil or fractionated coconut oil for 1,2,4-benzotriazine oxide as disclosed in U.S. Pat. No. 5,597,582 to Sanofi), or the like into the dosage forms for drug delivery has arisen.

In many cases the above substances are greasy, sticky or oily products. Incorporation of large amounts of such substances into pharmaceutical dosage forms have since long been known to cause technical problems. One of the problems has been to get pharmaceutically acceptable dry materials that are easy to handle and use as such or in later process steps.

Earlier ways to circumvent the problem include filling the greasy, oily or sticky substances as such into soft gelatin capsules, as for instance described in U.S. Pat. No. 5,589,455 (Han Mi Pharm.) where a concentrate for soft gelatin capsule filling comprising a cyclosporin and an oily component for improving the bioavailability is disclosed.

Many researchers have during the years described the advantage of using many small pellets (multiple unit) as a dosage form, with respect to their behaviour in vivo, i.e. especially with respect to their gastric emptying properties, see for instance Bogentoft et al, J. Clin. Pharmacol. 1978, 14, 351–5. Also e.g. Edgar et al describes advantages obtained with the use of a large number of pellets compared to a single unit, see Biopharmaceutics & Drug Disposition 1984, 5, 251–60. Risk for local irritation and accumulation of several doses due to constriction in the alimentary canal are also considered to be reduced, see McMahon F. G. et al. in The Lancet, Nov. 13, 1982, 1059–61.

To use complex coacervation microencapsulation is one way to circumvent the problem in line with the above findings. This method has been described by Jizomoto et al in Pharmaceutical Research vol. 10, No. 8, 1115–22. The method comprising formation of a surrounding coating layer consisting of two oppositely charged polymers forming an uncharged complex, is often associated with technical problems e.g. with respect to scaling-up, removal of residual reagents like hardening agents (e.g. glutaraldehyde) and solvents (e.g. isopropanol). The method may also be expensive due to many and complicated process steps, among other things necessiated by need of pH-adjustment, need of addition of antiadherents, need of particle separation step and need of solvent removal and enviromental considerations with regard to solvent handling, etc.

When administrering active drug together with absorption enhancers, it has earlier been proposed to fill the oily enhancer or enhancer dissolved in oil, together with drug in soft gelatin capsules, as by Adusumilli et al in U.S. Pat. No. 5,595,758.

Another more sofisticated way has been proposed by designing the dosage forms to have synchronized controlled release, i.e. sustained release, formulations to acertain that two components arrive at the absorption site at the right time, i.e. approximately simultaneously. See for instance Rubinstein et al in WO 95/34294 (Hamilton, Brook, Smith & Reynolds, P.C.) where an erodible hydrogel is used to serve as sustained oral delivery system, releasing small portions of drug and enhancer at the same time during a prolonged time intervall.

DESCRIPTION OF THE INVENTION

It has now been found that a drug delivery system for oral administration in solid dry form of greasy, oily or sticky (henceforward g/o/s) substance(s) and pharmaceutically active substance(s) or a pharmacetically active substance(s) which itself is/are g/o/s characterized by having a plurality of solid, polymeric matrix beads comprising considerable amounts of g/o/s substances and having fast release characteristics can overcome the drawbacks associated with previous systems and (when applicable) facilitate simultaneous administration of two components.

Thus, the present invention provides a new dosage form principle for incorporation of g/o/s materials and/or including pharmaceutically active substances, into particles of small up to moderate size which are easy to handle. The invention also enables the possibility to make multiple unit dosage systems thereof.

The present invention is directed to the approach of fast release, which will ensure that drug and absorption enhancer/solubilty enhancer is delivered to the desired site simultaneously and in as high concentration as possible, and to accomplish a better concentration gradient giving high drive force and enforcing the drug absorption possibilities. This is accomplished by using solid easily soluble polymers of polyethylene glycol, that will dissolve rapidly in the gastrointestinal system at the desired locus.

It is also one characteristic of the invention to have a considerable content of the greasy, oily or sticky materials in the produced particles, to ensure locally high concentrations in vivo.

By transforming the used polymer from the solid state to the liquid one, it is possible to emulsify or suspend drug and enhancers therein. After this procedure a suitable aliquot of the emulsion/suspension is separated and transferred back to solid state. This is done with all aliquots assuring transfer of all material to the solid state. If necessary, the emulsions may be stabilized by the addition of surfactants.

As fast release is required, all chemical treatment with hardening agents of the polymers, is outside the scope of this invention.

It has now been found that the disadvantages usually associated with particles having g/o/s materials incorporated in them have been overcome.

The oily substances incorporated may be but are not restricted to, pharmaceutically active agents, absorption enhancers or solubilizers.

DETAILED DESCRIPTION OF THE INVENTION

The pharmaceutical, solid, polymeric matrix beads for oral administration comprising considerable amounts of g/o/s pharmaceutically active substance(s) or pharmaceutically active substance(s) [g/o/s or not] plus such g/o/s substances, with fast release characteristics according to the invention are in this patent application considered to have fast release characteristics when they with an in-vitro dissolution test release not less than 60% w/w (preferably 70% w/w) of pharmaceutically active substance and g/o/s substance, or pharmaceutically active substance when the pharmaceutically active substance is the g/o/s substance, within 30 minutes or shorter. The calculation is based on water-free beads. For the g/o/s substances the dissolution rate is determined using USP apparatus No. 2 (paddle), operated at 100 rpm. The dissolution medium has a temperature of 37±0.5° C. Further there is a demand on the amount and art of dissolution medium, that it enables for the whole dose to be tested a non-retarded homogenous distribution of liberated g/o/s substance within the medium.

For the specific g/o/s substances shown in the examples, the medium disclosed in each example is the appropriate one.

For the pharmaceutically active substances the dissolution rate is determined using USP apparatus No. 2 (paddle), operated at 100 rpm. The dissolution medium has a temperature of 37±0.5° C. Further there is a demand on the amount and art of dissolution medium, that it enables for the whole dose to be tested, a non-retarded homogenous distribution of liberated drug within the medium (sink conditions).

For the specific pharmaceutically active substances shown in the examples, the medium disclosed in each example is the appropriate one.

It should be noted that for the one and same formulation different dissolution media might be chosen depending on the properties of the substances to be tested, i.e. if there are a g/o/s substance and a pharmaceutically active substance present in the formulation, depending on which one of these that is to be tested.

To have the desired handling characteristics, the solid polymeric beads, i.e. particles of the invention, are of small up to moderate size, that is having an average particle diameter from 0.1 mm to 10 mm, preferably from 0.25 to 3 mm. The shape of the beads are not restricted to a spherical form, the beads can also be of irregular shape.

With a considerable amount of the greasy, oily and/or sticky substance of the invention is considered from 15% w/w up to 70% /w/w, preferably 30% w/w to 70% w/w, most preferably 40% w/w to 70% w/w.

The rest of the drug delivery system comprises active drug (when the greasy/oily substance is not in itself the drug), polymeric matrix former, and if necessary surfactants, water and pharmaceutically acceptable excipients like e.g. pH-buffers, antioxidants, pigments or the like.

Drugs with a molecular weight lower than 1000 daltons and which can withstand a shorter heating period up to a maximum of 60–70° are considered to be usable in the invention and may be exemplified, but not restricted to thrombin inhibiting peptide drugs and dihydropyridine compounds. Particular examples of drugs are melagatran, inogatran, alendronate, felodipine, nifedipine and almokalant.

Polymeric materials functioning in the invention are solid, watersoluble polyethylene-glycols with an average molecular weight from 4000 (PEG 4000) up to 100000 (polyox N-10), preferably from 6000 up to 20000.

Polymeric materials functioning as sole matrix formers are polyethylene glycol polymers designated to have a molecular weight ranging from 4000 up to 20000, start and end value included. Non-exclusive examples from this group are PEG 4000, PEG 6000 and Carbowax 20M.

If considerations are taken to maintaining the desired fast release characteristics, it is also possible to use mixtures of polyethylene glycol polymers with different molecular weights as matrix formers. In this case the invention can be practised with polymers designated to have a molecular weight ranging from 4000 up to 100000, start and end value included.

To modify mechanical properties or/and to modify release characteristics of the matrix formulation, it might be appropriate to include even some liquid polyethylene glycols in a mixture with solid ones, provided that it is in such proportions that the resulting matrix beads become solid. In such cases, the invention can be practised with polymers designated to have a molecular weight ranging from 400 up to 100000, start and end value included. Non-exclusive examples from this group are PEG 400 and Polyox WSR N-10.

Examples of surfactants are, but not restricted to; polyoxyethylenated sorbitan esters (e.g. Tweens), sorbitan esters (e.g. Spans), polyoxyethylene esters (Myrjs, some Arlatones,) polyoxyethylenated hydrogenated castor oils (Cremophors), sodium laurylsulphate,.

Preparation of Matrix Beads

First, a transformation of the polymer from the solid state to the liquid one is performed, which may be accomplished by thermal treatment alone (e.g. polyethylene glycol) or by addition of melting point lowering compounds and thereafter thermal treatment. Sometimes addition of surfactants are beneficial, and they may be chosen among any pharmaceutically acceptable surfactants as long as the choice of amount and compound does not affect the dissolution properties required. The oily compound is added and emulsified. The drug (if not being the oily component) may be added to either the oily phase or the melted polymer phase or a combination thereof and may be dissolved or dispersed. After agitation suitable aliquots of the suspensions/emulsions may be produced by several techniques such as dropping, spraying, using centrifugal force techniques with rotating plates or nozzles. (Goodwin J. T., Sommerville G. R., Chem.Technol. 74; vol. 4 (10); pp 623–626).

By the choice of operating equipment and the process variables used, the obtained dropsize (aliquot size) will be controlled, and thereby the size of the later obtained congealed (and dried when desired and applicable) particles.

Transformation of the polymeric emulsions/suspensions aliquots/droplets from the liquid state to the solid one, is usually accomplished by congealing, and may be achieved in a non-solvent fluidizing medium, i.e. in non-solvent gases or liquids. The congealing may also take place on a powder bed.

After congealing, drying may be performed if desired and applicable.

Gases usable as fluidizing medium include; air, nitrogen, helium or other inert gases. If a fast congealing effect is desired the used gases may be used cooled to liquids, e.g. liquid nitrogen.

Liquids usable depends on their solubility properties, the general demand is that it should not dissolve the polymer or any considerable amounts of the in the embodiment included compounds. As a not generally working example liquid paraffin oil may be given. This is as the liquids to use have to be carefully selected for each new embodiment of the invention.

As powders for the powder bed dropping may be used those that do not dissolve in the emulsion/suspension dropped thereupon or in which the emulsion/suspension is not adsorbed and do not affect the release rate characteristics of the formed particles. Example given is corn starch, potatoe starch, sodium aluminium silicate, talc, crosslinked polyvinylpyrrolidone, calcium phosphate, sodium starch glycolate.

WORKING EXAMPLES

Example 1

Beads of polyethylene glycol 6000 containing felodipine and Cremophor® RH 40. The content of Cremophor® RH 40 was 51% w/w on dry basis.

| | |
|---|---|
| Felodipine | 0.32 g |
| Cremophor ® RH 40 | 4.43 g |
| polyethylene glycol 6000 | approx. 4.0 g |

The polyethylene glycol was melted in a beaker at a temp. between 50–60° C.

In a separate beaker the creamy, sticky substance Cremophor® RH 40 was heated to accomplish liquefaction. A magnetic teflon coated stirrer was added in the beaker. This was placed on a plate with heating and stirring control. The felodipine was dissolved in the liquefied Cremophor® during mild agitation.

The melted polyethylene glycol was poured into the beaker containing Cremophor® RH 40 and felodipine. After agitation the melted mixture formed was dripped on a bed of corn starch powder, and left to congeal until hardened.

The powder bed with congealed beads was transferred to a 0.7 mm sieve and the corn starch was separated from the beads.

Collected beads were analysed with regard to dissolution of felodipine using USP dissolution apparatus No. 2 (paddle), operated at 100 rpm. The dissolution medium used, having a temperature of 37° C., was phosphate buffer pH 6.5 containing 0.4 per cent of cetyltrimethylammonium bromide. The amount of felodipine released was determined by UV-spectrometry.

After 30 minutes the amount of felodipine dissolved was 95% (as average, n=3) of the found content. The particles were visually observed during the dissolution and after 20 min the particles were completely dissolved (showing that Cremophor® RH 40 was completely dissolved).

Example 2

Beads of polyethylene glycol 6000 and polyethylene glycol 400 containing felodipine and Cremophor® RH 40. The content of Cremophor® RH 40 was 41% w/w on dry basis.

| | |
|---|---|
| Felodipine | 0.32 g |

| -continued | |
|---|---|
| Cremophor ® RH 40 | 4.43 g |
| polyethylene glycol 6000 | 5.8 g |
| polyethylene glycol 400 | 0.2 g |
| Polyox ® N-10 | 0.1 g |

Polyethylene glycol 6000 is melted in a beaker at a temp. between 50–60° C. and polyethylene glycol 400 is added.

In a separate beaker the creamy, sticky substance Cremophor® RH 40 is heated to accomplish liquefaction. A magnetic teflon coated stirrer is added in the beaker. This is placed on a plate with heating and stirring control. The felodipine is dissolved in the liquefied Cremophor® during mild agitation.

The melted mixture of polyethylene glycols is poured into the beaker containing Cremophor® RH 40 and felodipine. After agitation the melted mixture formed is dripped on a bed of corn starch powder, and left to congeal until hardened.

The powder bed with congealed beads is transferred to a 0.7 mm sieve and the corn starch is separated from the beads.

Example 3

Beads of polyethylene glycol 6000 containing melagatran and Akoline® MCM. The content of Akoline® MCM was 43% w/w on dry basis.

| | |
|---|---|
| Melagatran | 0.26 g |
| polyethylene glycol 6000 | 5.0 g |
| Tween ® 20 | 0.6 g |
| Akoline ® MCM | 4.4 g |

The components were fused together during stirring with a magnetic teflon coated stirrer on a plate with heating and stirring control.

After fusing, the mass was dripped on a bed of corn starch powder, and left to congeal.

After approx. 30 minutes the powder bed with congealed beads was transferred to a 0.5 mm sieve and the corn starch was separated from the beads.

Collected beads were analysed with regard to dissolution of Akoline® MCM and melagatran using a USP dissolution apparatus No. 2 (paddle), operated at 100 rpm. The dissolution medium used, having a temperature of 37° C., was phosphate buffer pH 6.8 with additions of 2 mM lecithin and 5 mM taurocholate to make the sample uptake homogeneous. The sample components were separated by liquid chromatography. The amount of Akoline® released was determined using a light scattering detector and the amount of melagatran released was determined by UV-spectrometry.

After 30 minutes the amount of Akoline® dissolved was 71% (as average, n=2) of the found content. The amount of melagatran dissolved after 30 minutes was 97% (as average, n=2) of the found content.

Example 4

Beads of polyethylene glycol 6000 containing alnokalant 48% w/w on dry basis.

| | |
|---|---|
| Almokalant | 4.63 g |
| polyethylene glycol 6000 | 4.91 g |

The polyethylene glycol was melted in a beaker at a temp. between 50–60° C.

The melted polyethylene glycol was poured into the beaker containing almokalant After agitation the melted mixture formed was dripped on a bed of corn starch powder, and left to congeal until hardened.

The powder bed with congealed beads was transferred to a 1.0 mm sieve and the corn starch was separated from the beads.

Collected beads were analysed with regard to dissolution of almokalant using USP dissolution apparatus No. 2 (paddle), operated at 100 rpm. The dissolution medium used, having a temperature of 37° C., was phosphate buffer pH 6.8. The amount of almokalant released was determined by UV-spectrometry.

After 30 minutes the amount of almokalant dissolved was 74% (as average, n=2) of the found content.

Example 5

Beads obtained in example 1 were filled into hard gelatine capsules of size 3. Each capsule as filled with 0.15 g beads. This corresponded to a capsule content of 5 mg felodipine.

What is claimed is:

1. A dry, solid, fast release drug delivery composition which comprises:
   (i) a component consisting essentially of at least one pharmaceutically active substance selected from the group consisting of thrombin inhibiting peptide drugs, alendronate, and almokalant, the composition comprising from 15 wt % to 70 wt % of the component, and
   (ii) a polymeric matrix wherein the sole matrix forming material is a polyethylene glycol or a mixture of polyethylene glycols, wherein the polyethylene glycol or the mixture is solid at ambient temperature,
      said composition being in the form of a plurality of beads and having fast release characteristics defined by in-vitro dissolution test release within 30 minutes of not less than 60% w/w of the component (i).

2. The drug delivery composition according to claim 1, wherein the polyethylene glycol has a molecular weight of from 4000 to 20000.

3. The drug delivery composition according to claim 1, wherein the polyethylene glycols of the mixture have a molecular weight from 4000 to 100000.

4. The drug delivery composition according to claim 1, wherein the polyethylene glycols of the mixture have a molecular weight from 400 to 100000, provided that they are in such proportions that the resulting matrix beads become solid at ambient temperature.

5. The drug delivery composition according to any one of the preceding claims wherein the polymeric matrix beads have a particle size of 0.1–10 mm.

6. The drug delivery composition according to any one of claims 1–4, wherein the polymeric matrix beads have a particle size of 0.25–3 mm.

7. The drug delivery composition according to claim 1, wherein the pharmaceutically active substance has a molecular weight less than 1000 dalton.

8. The drug delivery composition according to claim 1, wherein the thrombin inhibiting peptide drug is melagatran.

9. A process for the preparation of a dry, solid, fast release drug delivery composition which comprises:
   (i) a component consisting essentially of at least one pharmaceutically active substance selected from the group consist of thrombin inhibiting peptide drugs, alendronate, and almokalant, the composition comprising from 15 wt % to 70 wt % of the component, and
   (ii) a polymeric matrix wherein the sole matrix forming material is a polyethylene glycol or a mixture of polyethylene glycols,
   wherein the process consists essentially of the steps of:
      a) transforming a polyethylene glycol or a mixture of polyethylene glycols from a solid state to a liquid state, the polyethylene glycol or the mixture of polyethylene glycols being solid at ambient temperature;
      b) adding the at least one pharmaceutically active substance;
      c) preparing an emulsion/suspension of the mixture of the components used in step (a) and the components added in step (b); and
      d) transforming suitable aliquots/droplets of the emulsion/suspension to form a plurality of beads in the solid state,
   said beads forming the composition and having fast release defined by in-vitro dissolution test release within 30 minutes of not less than 60% w/w of the component (i).

10. The drug delivery composition according to claim 1, wherein the polymeric matrix includes one or more optional ingredients selected from the group consisting of surfactants, water, pH buffers, antioxidants and pigments.

11. The drug delivery composition according to claim 1, wherein the dissolution rate is determined under test conditions comprising test beads which are free of water, a dissolution medium having a temperature of 36.5–37.5° C. and operation of a USP apparatus No. 2 at 100 rpm.

12. The drug delivery composition according to claim 1, wherein the thrombin inhibiting peptide drug is inogatran.

13. The drug delivery composition according to claim 1, wherein the pharmaceutically active substance is a greasy, oily or sticky substance.

14. The process according to claim 9, wherein the thrombin inhibiting peptide drug is melagatran or inogatran.

15. The process according to claim 9, wherein the pharmaceutically active substance is a greasy, oily or sticky substance.

* * * * *